(12) United States Patent
Ren et al.

(10) Patent No.: US 9,811,758 B2
(45) Date of Patent: *Nov. 7, 2017

(54) MATCHING GEOMETRY GENERATION AND DISPLAY OF MAMMOGRAMS AND TOMOSYNTHESIS

(71) Applicant: Hologic, Inc., Bedford, MA (US)

(72) Inventors: Baorui Ren, Andover, MA (US); Christopher Ruth, Boxford, MA (US); Andrew P. Smith, Lexington, MA (US); Kevin Wilson, Waltham, MA (US); Jay A. Stein, Boston, MA (US)

(73) Assignee: HOLOGIC, INC., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/744,930

(22) Filed: Jun. 19, 2015

(65) Prior Publication Data

US 2015/0317538 A1 Nov. 5, 2015

Related U.S. Application Data

(63) Continuation of application No. 14/263,216, filed on Apr. 28, 2014, now Pat. No. 9,084,579, which is a
(Continued)

(51) Int. Cl.
G06K 9/00 (2006.01)
G06K 9/62 (2006.01)
(Continued)

(52) U.S. Cl.
CPC ............ *G06K 9/6201* (2013.01); *A61B 6/502* (2013.01); *G06T 3/0006* (2013.01); *G06T 7/30* (2017.01);
(Continued)

(58) Field of Classification Search
CPC .. G06T 3/40; G06T 19/00; G06T 3/00; G01N 2015/1447; G01N 2015/1452; G02B 21/367
(Continued)

(56) References Cited

U.S. PATENT DOCUMENTS 3,502,878 A 3/1970 Stewart
3,863,073 A 1/1975 Wagner
(Continued)

FOREIGN PATENT DOCUMENTS

EP 0775467 A1 5/1997
EP 0982001 A1 3/2000
(Continued)

OTHER PUBLICATIONS

Cole, Elodia, et al., "The Effects of Gray Seale Image Processing on Digital Mammography Interpretation Performance", Academic Radiology, vol. 12, No. 5, pp. 585-595, May 2005.
(Continued)

*Primary Examiner* — Ali Bayat

(57) ABSTRACT

A method and a system for using tomosynthesis projection images of a patient's breast to reconstruct slice tomosynthesis images such that anatomical structures that appear superimposed in a mammogram are at conforming locations in the reconstructed images.

20 Claims, 5 Drawing Sheets

Front View

Related U.S. Application Data continuation of application No. 13/418,851, filed on Mar. 13, 2012, now Pat. No. 8,712,127, which is a continuation of application No. 12/535,343, filed on Aug. 4, 2009, now Pat. No. 8,155,421, which is a continuation of application No. 11/667,650, filed as application No. PCT/US2005/041941 on Nov. 15, 2005, now Pat. No. 7,702,142.

(60) Provisional application No. 60/628,516, filed on Nov. 15, 2004.

(51) Int. Cl.
*G06T 3/00* (2006.01)
*G06T 11/00* (2006.01)
*A61B 6/00* (2006.01)
*G06T 11/60* (2006.01)
*G06T 7/30* (2017.01)

(52) U.S. Cl.
CPC ............ *G06T 11/006* (2013.01); *G06T 11/60* (2013.01); *G06T 2207/10081* (2013.01); *G06T 2207/30068* (2013.01)

(58) Field of Classification Search
USPC ............................................................ 382/131
See application file for complete search history.

(56) References Cited

U.S. PATENT DOCUMENTS

| | | | |
|---|---|---|---|
| 3,971,950 A | 7/1976 | Evans et al. | |
| 4,160,906 A | 7/1979 | Daniels et al. | |
| 4,310,766 A | 1/1982 | Finkenzeller et al. | |
| 4,496,557 A | 1/1985 | Malen et al. | |
| 4,559,641 A | 12/1985 | Caugant et al. | |
| 4,706,269 A | 11/1987 | Reina et al. | |
| 4,744,099 A | 5/1988 | Huettenrauch et al. | |
| 4,773,086 A | 9/1988 | Fujita et al. | |
| 4,773,087 A | 9/1988 | Plewes | |
| 4,819,258 A | 4/1989 | Kleinman et al. | |
| 4,821,727 A | 4/1989 | Levene et al. | |
| 4,969,174 A | 11/1990 | Scheid et al. | |
| 4,989,227 A | 1/1991 | Tirelli et al. | |
| 5,018,176 A | 5/1991 | Romeas et al. | |
| RE33,634 E | 7/1991 | Yanaki | |
| 5,029,193 A | 7/1991 | Saffer | |
| 5,051,904 A | 9/1991 | Griffith | |
| 5,078,142 A | 1/1992 | Siczek et al. | |
| 5,163,075 A | 11/1992 | Lubinsky et al. | |
| 5,164,976 A | 11/1992 | Scheid et al. | |
| 5,199,056 A | 3/1993 | Darrah | |
| 5,240,011 A | 8/1993 | Assa | |
| 5,289,520 A | 2/1994 | Pellegrino et al. | |
| 5,359,637 A | 10/1994 | Webbe | |
| 5,365,562 A | 11/1994 | Toker | |
| 5,415,169 A | 5/1995 | Siczek et al. | |
| 5,426,685 A | 6/1995 | Pellegrino et al. | |
| 5,452,367 A | 9/1995 | Bick et al. | |
| 5,506,877 A | 4/1996 | Niklason et al. | |
| 5,526,394 A | 6/1996 | Siczek et al. | |
| 5,539,797 A | 7/1996 | Heidsieck et al. | |
| 5,553,111 A | 9/1996 | Moore et al. | |
| 5,592,562 A | 1/1997 | Rooks | |
| 5,594,769 A | 1/1997 | Pellegrino et al. | |
| 5,596,200 A | 1/1997 | Sharma et al. | |
| 5,598,454 A | 1/1997 | Franetzki et al. | |
| 5,609,152 A | 3/1997 | Pellegrino et al. | |
| 5,627,869 A | 5/1997 | Andrew et al. | |
| 5,657,362 A | 8/1997 | Giger et al. | |
| 5,668,889 A | 9/1997 | Hara | |
| 5,719,952 A | 2/1998 | Rooks | |
| 5,735,264 A | 4/1998 | Siczek et al. | |
| 5,769,086 A | 6/1998 | Ritchart et al. | |
| 5,803,912 A | 9/1998 | Siczek et al. | |
| 5,818,898 A | 10/1998 | Tsukamoto et al. | |
| 5,828,722 A | 10/1998 | Ploetz et al. | |
| 5,872,828 A | 2/1999 | Niklason et al. | |
| 5,878,104 A | 3/1999 | Ploetz | |
| 5,896,437 A | 4/1999 | Ploetz | |
| 5,986,662 A | 11/1999 | Argiro et al. | |
| 6,005,907 A | 12/1999 | Ploetz | |
| 6,022,325 A | 2/2000 | Siczek et al. | |
| 6,075,879 A | 6/2000 | Roehrig et al. | |
| 6,091,841 A | 7/2000 | Rogers et al. | |
| 6,137,527 A | 10/2000 | Abdel-Malek et al. | |
| 6,141,398 A | 10/2000 | He et al. | |
| 6,149,301 A | 11/2000 | Kautzer et al. | |
| 6,175,117 B1 | 1/2001 | Komardin et al. | |
| 6,196,715 B1 | 3/2001 | Nambu et al. | |
| 6,216,540 B1 | 4/2001 | Nelson et al. | |
| 6,219,059 B1 | 4/2001 | Argiro | |
| 6,233,473 B1 | 5/2001 | Shepherd et al. | |
| 6,243,441 B1 | 6/2001 | Zur | |
| 6,256,370 B1 | 7/2001 | Yavuz | |
| 6,272,207 B1 | 8/2001 | Tang | |
| 6,289,235 B1 | 9/2001 | Webber et al. | |
| 6,292,530 B1 | 9/2001 | Yavus et al. | |
| 6,327,336 B1 | 12/2001 | Gingold et al. | |
| 6,341,156 B1 | 1/2002 | Baetz et al. | |
| 6,375,352 B1 | 4/2002 | Hewes et al. | |
| 6,411,836 B1 | 6/2002 | Patel et al. | |
| 6,415,015 B2 | 7/2002 | Nicolas et al. | |
| 6,442,288 B1 | 8/2002 | Haerer et al. | |
| 6,459,925 B1 | 10/2002 | Nields et al. | |
| 6,501,819 B2 | 12/2002 | Unger et al. | |
| 6,556,655 B1 | 4/2003 | Chichereau et al. | |
| 6,597,762 B1 | 7/2003 | F errant et al. | |
| 6,611,575 B1 | 8/2003 | Alyassin et al. | |
| 6,620,111 B2 | 9/2003 | Stephens et al. | |
| 6,626,849 B2 | 9/2003 | Huitema et al. | |
| 6,633,674 B1 | 10/2003 | Barnes et al. | |
| 6,638,235 B2 | 10/2003 | Miller et al. | |
| 6,647,092 B2 | 11/2003 | Eberhard et al. | |
| 6,744,848 B2 | 6/2004 | Stanton et al. | |
| 6,748,044 B2 | 6/2004 | Sabol et al. | |
| 6,751,285 B2 | 6/2004 | Eberhard et al. | |
| 6,758,824 B1 | 7/2004 | Miller et al. | |
| 6,813,334 B2 | 11/2004 | Koppe et al. | |
| 6,882,700 B2 | 4/2005 | Wang et al. | |
| 6,885,724 B2 | 4/2005 | Li et al. | |
| 6,912,319 B1 | 6/2005 | Barnes et al. | |
| 6,940,943 B2 | 9/2005 | Claus et al. | |
| 6,978,040 B2 | 12/2005 | Berestov | |
| 6,999,554 B2 | 2/2006 | Mertelmeier | |
| 7,025,725 B2 | 4/2006 | Dione et al. | |
| 7,110,490 B2 * | 9/2006 | Eberhard | A61B 6/025 378/197 |
| 7,110,502 B2 | 9/2006 | Tsuji | |
| 7,123,684 B2 | 10/2006 | Jing et al. | |
| 7,127,091 B2 | 10/2006 | Op De Beek et al. | |
| 7,142,633 B2 | 11/2006 | Eberhard et al. | |
| 7,245,694 B2 | 7/2007 | Jing et al. | |
| 7,315,607 B2 | 1/2008 | Ramsauer | |
| 7,319,735 B2 | 1/2008 | Defreitas et al. | |
| 7,323,692 B2 | 1/2008 | Rowlands et al. | |
| 7,430,272 B2 | 9/2008 | Jing et al. | |
| 7,443,949 B2 | 10/2008 | Defreitas et al. | |
| 7,630,533 B2 | 12/2009 | Ruth et al. | |
| 7,702,142 B2 * | 4/2010 | Ren | G06T 3/0006 378/23 |
| 8,712,127 B2 | 4/2014 | Ren et al. | |
| 9,084,579 B2 | 7/2015 | Ren et al. | |
| 2001/0038681 A1 | 11/2001 | Stanton et al. | |
| 2001/0038861 A1 | 11/2001 | Hsu et al. | |
| 2002/0012450 A1 | 1/2002 | Tsujii | |
| 2002/0050986 A1 | 5/2002 | Inoue et al. | |
| 2002/0075997 A1 | 6/2002 | Unger et al. | |
| 2003/0018272 A1 | 1/2003 | Treado et al. | |
| 2003/0073895 A1 | 4/2003 | Nields et al. | |
| 2003/0095624 A1 | 5/2003 | Eberhard et al. | |
| 2003/0194050 A1 | 10/2003 | Eberhard et al. | |
| 2003/0194051 A1 | 10/2003 | Wang et al. | |

(56) References Cited

U.S. PATENT DOCUMENTS

| | | |
|---|---|---|
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0008809 A1 | 1/2004 | Webber |
| 2004/0066882 A1 | 4/2004 | Eberhard et al. |
| 2004/0066884 A1 | 4/2004 | Hermann Claus et al. |
| 2004/0066904 A1 | 4/2004 | Eberhard et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0105679 A1 | 5/2005 | Wu et al. |
| 2005/0113681 A1* | 5/2005 | DeFreitas ............... A61B 6/502 600/426 |
| 2005/0113715 A1 | 5/2005 | Schwindt et al. |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0155209 A1 | 7/2006 | Miller et al. |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0130979 A1 | 6/2008 | Ren et al. |
| 2009/0003519 A1 | 1/2009 | Defreitas et al. |
| 2009/0010384 A1 | 1/2009 | Jing et al. |
| 2009/0080594 A1 | 3/2009 | Brooks et al. |
| 2009/0080602 A1 | 3/2009 | Brooks et al. |
| 2009/0135997 A1 | 5/2009 | Defreitas et al. |
| 2009/0268865 A1 | 10/2009 | Ren et al. |
| 2009/0296882 A1 | 12/2009 | Gkanatsios et al. |
| 2009/0304147 A1 | 12/2009 | Jing et al. |
| 2010/0054400 A1 | 3/2010 | Ren et al. |
| 2010/0086188 A1 | 4/2010 | Ruth et al. |
| 2010/0135558 A1 | 6/2010 | Ruth et al. |
| 2010/0195882 A1 | 8/2010 | Ren et al. |
| 2010/0226475 A1 | 9/2010 | Smith et al. |

FOREIGN PATENT DOCUMENTS

| | | |
|---|---|---|
| EP | 1428473 A2 | 6/2004 |
| WO | WO 90/05485 | 5/1990 |
| WO | WO 98/16903 | 4/1998 |
| WO | WO 00/51484 | 9/2000 |
| WO | WO 03/020114 A2 | 3/2003 |
| WO | WO 2005/051197 A1 | 6/2005 |
| WO | WO 2005110230 A1 | 11/2005 |
| WO | WO 2005 112767 A1 | 12/2005 |
| WO | WO 2006/055830 A2 | 5/2006 |
| WO | WO 2006/058160 A2 | 6/2006 |

OTHER PUBLICATIONS

Digital Clinical Reports, Tomosynthesis, GE Brochure 98/5493, Nov. 1998.

Dobbins JT et al. "Digital x-ray tomosynthesis: current state of the art and clinical potential" Physics in Medicine and Biology vol. 48, No. 19, pp. 65-81 (2003).

Essentials for life: Senographe Essential Full-Field Digital Mammography System, GE Health-care Brochure, MM-0132-05.06-ENUS, 2006.

Federica Pediconi et al., "Color-coded automated signal intensity curve for detection and characterization of breast lesions: Preliminary evaluation of a new software for MR-based breast imaging", International Congress Series 1281 (2005) 1081-1086.

Filtered Back Projection, (NYGREN) published May 8, 2007;URL: http://web.archive.org/web/1999101013 I 715/http://www.owlnet.rice.edu/-elec539/Projects97/cult/node2.html.

Grant, DG, "Tomosynthesis, a three dimensional imagine technique", IEEE Trans. Biomed Engineering, vol. BME-19, #1, Jan. 1972, pp. 20-28.

Heang-Ping Chan et al., "ROC study of the effect of stereoscopic imaging on assessment of breast lesions", Medical Physics, vol. 32, No. 4, Apr. 2005.

Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.

Lorad Selenia Document B-BI-SEO US/Intl (May 2006) copyright Hologic 2006.

Mammographic Accreditation Phantom, http://www.cirsinc.com/pdfs/015cp.pdf.

May 9, 2011 European search report in connection with counterpart European Patent Application No. 05 82 4734.

PCT International Search Report and Written Opinion in International Application PCT/US2005/041941, dated Sep. 25, 2008, 6 pgs.

Senographe 700 & SOOT (GE); 2-page download on Jun. 22, 2006 from www.gehealthcare.com/inen/rad/whe/products/mswh800t.html.; Figures 1-7 on 4 sheets relateral shift compression paddle.

Smith, A., "Fundamentals of Breast Tomosynthesis", White Paper, Hologic Inc., WP-00007, Jun. 2008.

\* cited by examiner

MATCHING GEOMETRY GENERATION AND DISPLAY OF MAMMOGRAMS AND TOMOSYNTHESIS

CROSS REFERENCE TO RELATED APPLICATIONS

This application is a continuation of U.S. application Ser. No. 14/263,216, now U.S. Pat. No. 9,084,579, filed Apr. 28, 2014; which is a continuation of U.S. application Ser. No. 13/418,851, now U.S. Pat. No. 8,712,127, filed Mar. 13, 2012; which is a continuation application of U.S. application Ser. No. 12/535,343, now U.S. Pat. No. 8,155,421, filed Aug. 4, 2009; which is a continuation application of U.S. application Ser. No. 11/667,650; now U.S. Pat. No. 7,702,142, filed Nov. 30, 2007; which is a National Stage Application of PCT/US2005/041941, filed Nov. 15, 2005; which claims priority to and the benefit of U.S. Provisional Application No. 60/628,516, now expired, filed Nov. 15, 2004; the disclosures of which are hereby incorporated by reference herein in their entireties.

FIELD

This patent specification is in the field of x-ray imaging of patients for screening or other purposes, and more specifically is directed to methods and systems for generating and displaying mammograms and tomosynthesis x-ray images in ways that improve their usefulness.

BACKGROUND

Breast cancer remains a significant threat to women's health. X-ray mammograms have long been a standard in screening patients for breast cancer or other abnormalities and also are widely used in diagnosis and treatment planning. X-ray mammography typically records the breast image on x-ray film but more recently digital x-ray image receptors have come into use, as in the Selenia™ mammography system available from Hologic Inc. of Bedford, Mass. and its division Lorad of Danbury, Conn. For mammograms, a cone-shaped or pyramid-shaped x-ray beam passes through the compressed breast and forms a two-dimensional projection image. Any one of a number of orientations can be used, such as cranial-caudal (CC) or MLO (mediolateral-oblique) orientation. More recently, breast x-ray tomosynthesis has been proposed. The technology typically involves taking two-dimensional (2D) projection images of the immobilized breast at each of a number of angles of the x-ray beam relative to the breast and processing the resulting x-ray measurements to reconstruct images of breast slices that typically are in planes transverse to the x-ray beam axis, such as parallel to the image plane of a mammogram of the same breast. The range of angles is substantially less than in computerized tomography, i.e. substantially less than 180°, e.g. ±15°. Tomosynthesis technology is described in U.S. patent application Ser. No. 10/723,486 filed Nov. 26, 2003; a prototype of a unit with at least some of the described features was shown at the 2003 Radiological Society of North America meeting in Chicago, Ill. Additional prototypes are in clinical testing in this country as of the filing of this patent specification. Other approaches to tomosynthesis also have been proposed: see, e.g., U.S. Pat. Nos. 4,496,557, 5,051,904, 5,359,637, 6,289,235, and 6,647,092, published U.S. Patent Applications Nos. 2001/0038861, 2004/066882, 2004/0066884, and 2004/0066904, and Digital Clinical Reports, Tomosynthesis (GE Brochure 98-5493, November/1998). How to reconstruct tomosynthesis images is discussed in DG Grant, "Tomosynthesis: a three-dimensional imaging technique", IEEE Trans. Biomed. Engineering, Vol BME-19, #1, (January 1972), pp 20-28. The patents, applications, brochures, and article cited above are hereby incorporated by reference in this patent specification as though fully set forth herein.

In clinical use, it can be desirable for a number of reasons to assess both tomosynthesis images and conventional mammograms of the patient's breasts. For example, the decades of conventional mammograms have enabled medical professionals to develop valuable interpretation expertise. Mammograms may offer good visualization of microcalcifications, and can offer higher spatial resolution compared with tomosynthesis. Tomosynthesis images may have different desirable characteristics—e.g., they may offer better visualization of structures that can be obscured by overlying or underlying tissue in a conventional mammogram. However, the inventors named herein have recognized that a challenge arises in assessing tomosynthesis images, either alone or in conjunction with mammograms of the same breast. Tomosynthesis images tend to look different from mammograms in that a given tomosynthesis image may not show anatomical structure seen in a mammogram or in another tomosynthesis image of the same breast; and, to the extent a tomosynthesis image shows structure that also is seen in the mammogram or in another tomosynthesis image, that structure may be at different relative places in the images. This can make it difficult to apply to tomosynthesis images the expertise built over years of experience reading mammograms, and difficult to visualize and assess the same structure from the different types of images. For these and other reasons, the inventors believe that a need exists for further improvements in the generation and presentation of such images to make them more useful to health professionals.

SUMMARY

The disclosed process and system generate and display tomosynthesis slice images of a patient's breast such that an object in the breast is at same or at least matching relative places in each slice image in which it is visible and, preferably, also at the same or at least matching place as in a conventional mammogram of the same breast. To achieve this, the method and system obtain 2D x-ray projection data for tomosynthesis images and, preferably, at least one 2D x-ray projection mammogram of a patient's breast, preferably using in each case a cone-shaped or pyramid-shaped imaging x-ray beam, and generate tomosynthesis images such that they conform to the same geometric coordinate system and, preferably, to the same coordinate system as a 2D projection mammogram. As a result, anatomical structures appear at geometrically matching or corresponding places in such tomosynthesis images and, preferably, in the mammogram. The tomosynthesis images can be generated in a two-step computer-implemented process that first reconstructs tomosynthesis images in an initial coordinate system in which objects are not or may not be at matching positions in different tomosynthesis images or in the mammogram, and then projects those images into another coordinate system, such as the coordinate system of the mammogram. Alternatively, the reconstruction can directly generate tomosynthesis images that match the appropriate coordinate system, e.g. the cone beam geometry of the mammogram. Still alternatively, the cone-shaped or pyramid-shaped beam can be simulated by scanning the breast with a fan-shaped x-ray beam or a beam having some other geometry. The term x-ray beam as used in this patent specification includes such simulated cone-shaped or pyramid-shaped beams.

DETAILED DESCRIPTION OF PREFERRED EMBODIMENTS

Figure 1A:
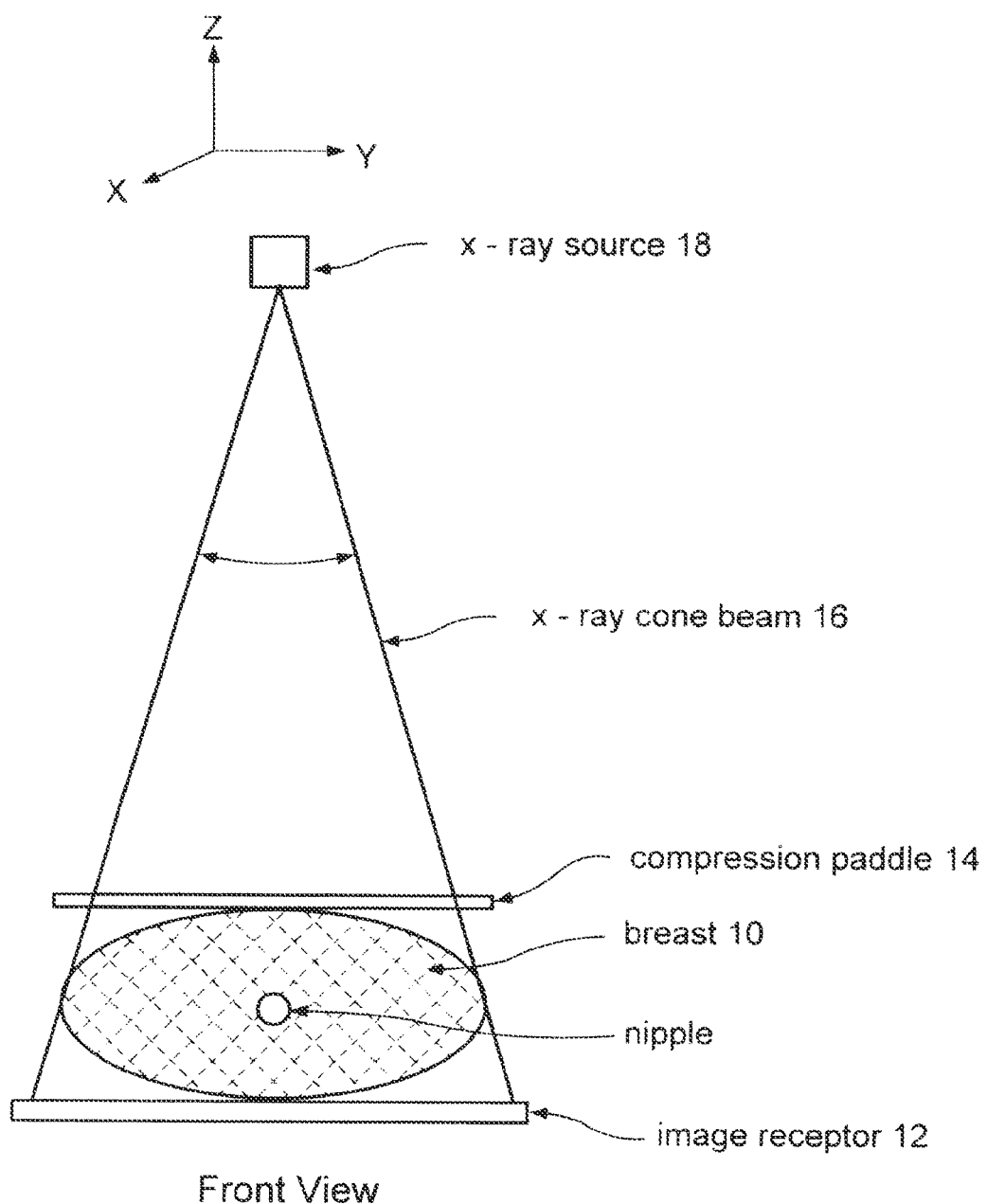
FIGS. 1a and 1b illustrate in simplified form an example of geometry used in obtaining x-ray mammograms and x-ray tomosynthesis measurements.
Figure 1B:
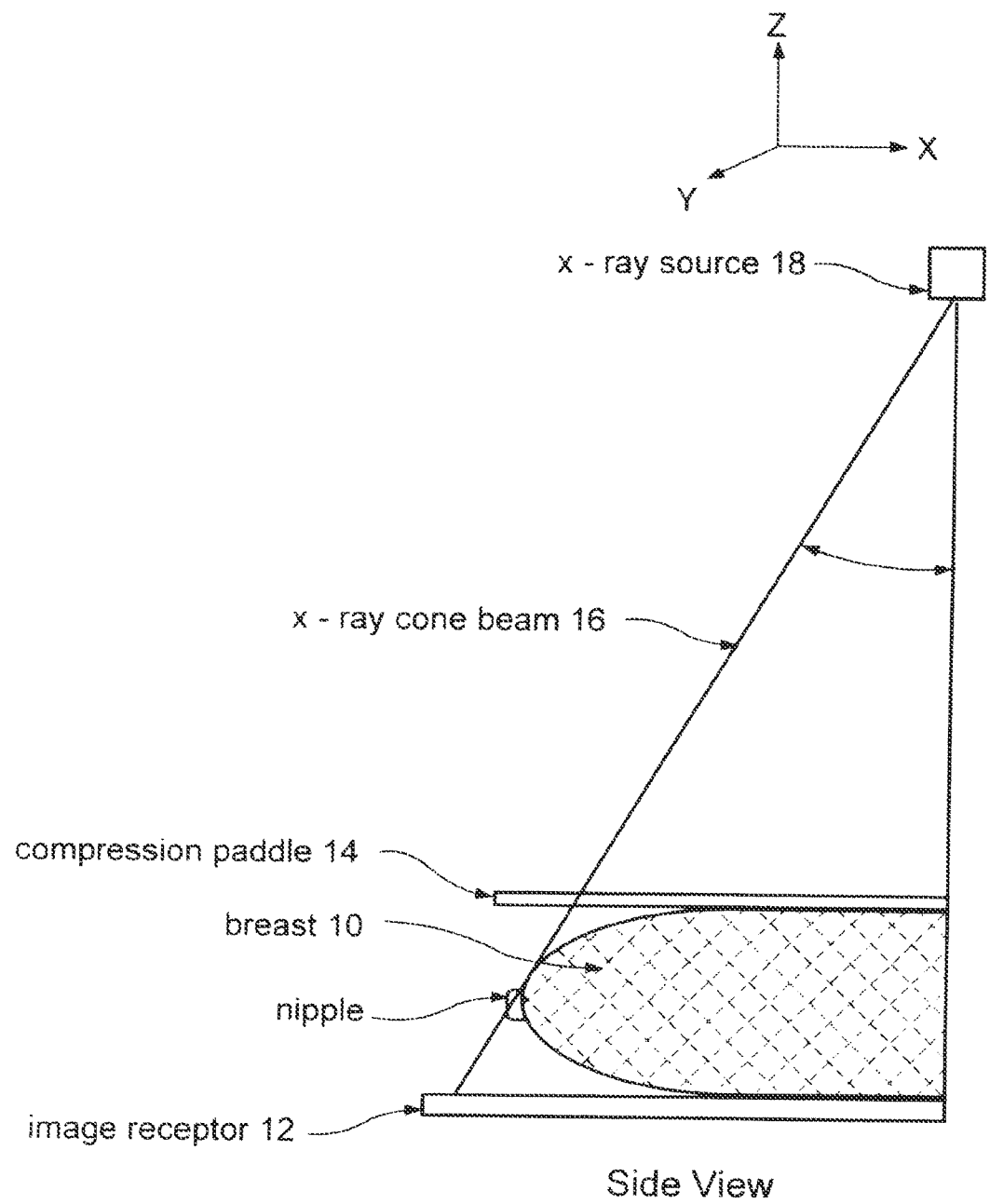

FIGS. 1a and 1b illustrate in simplified view an example of geometry for CC (cranial-caudal) imaging of a patient's breast 10. Breast 10 is compressed between an image receptor 12, such as a flat panel digital imager, and a compression paddle 14, and is imaged with a cone-shaped or pyramid-shaped x-ray beam 16 from an x-ray source 18. FIG. 1a illustrates a front view where the long axis of the compressed breast 10 is normal to the sheet, and FIG. 1b illustrates a side view where the long axis of the breast is in the plane of the sheet and where the patient's chest (not shown) is to the right of the illustrated geometry. Respective coordinate systems are shown above FIGS. 1a and 1b. In pertinent respect, the illustrated geometry is similar to that used in the Selenia™ mammography system identified above as well as in the tomosynthesis system disclosed in said patent application Ser. No. 10/723,486. As is known, the breast can be compressed and imaged in other orientations as well.

Figure 2:
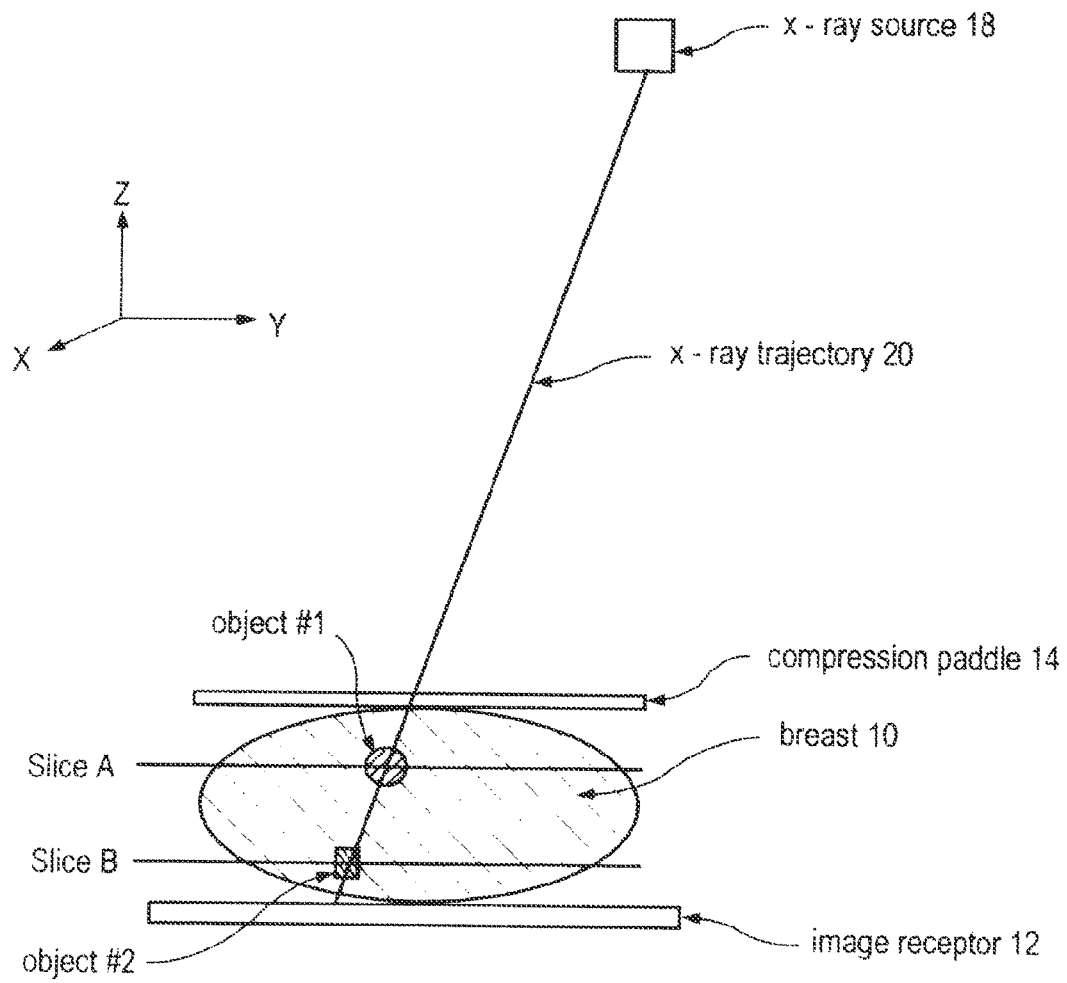
FIG. 2 illustrates image planes of a mammogram and tomosynthesis slice images.

FIG. 2 illustrates the same geometry as FIG. 1b, and the same coordinate system, except that it highlights a single raypath or x-ray trajectory 20 rather than illustrate the entire x-ray beam 16. In addition, FIG. 2 illustrates two objects in breast 10, object #1 at slice A and object #2 at slice B. The term object is used here to refer to any structure that can be imaged in a mammogram or a tomosynthesis image, such as a lesion in the breast, and the term slice is used to refer to a layer of the breast of a finite thickness, e.g. thickness in the z-direction, that is less than the total breast thickness. For example, a slice can be a few mm thick, or thinner or thicker.

Figure 3A:
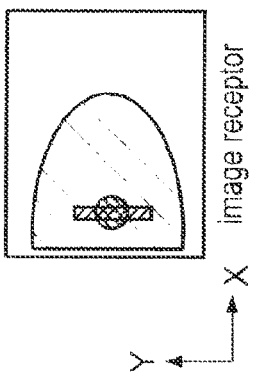
FIGS. 3a, 3b, and 3c illustrate, respectively, a conventional mammogram and two tomosynthesis slice images, where two objects that are at different heights in the breast appear superimposed in the mammogram but at different relative locations in the tomosynthesis slice images.
Figure 3B:
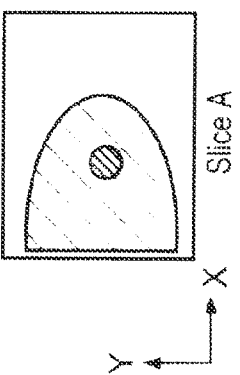
Figure 3C:
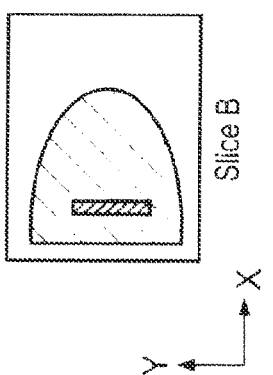

In tomosynthesis images, the same objects #1 and #2 can appear at different locations relative to other structure in the breast as compared with a mammogram of the same breast, as illustrated in FIGS. 3a-3c. FIG. 3a illustrates a mammogram that can be obtained with the geometry of FIG. 2, while FIGS. 3b and 3c illustrate tomosynthesis images of slices A and B, respectively, obtained with a system as disclosed in said application Ser. No. 10/723,486. Because objects #1 and #2 are along the same x-ray trajectory 20, they appear superimposed in the mammogram of FIG. 3a. However, because x-ray trajectory 20 is not normal to the image plane of receptor 12, as is the general case with x-ray trajectories when using such cone-beam or pyramid-beam x-ray geometry, the two objects appear at different xy locations in the tomosynthesis images of FIGS. 3b and 3c. These tomosynthesis images can be conceptualized as vertical projections of slices A and B onto the image plane of the mammogram, e.g. the image plane of x-ray receptor 12. Another way to conceptualize such a tomosynthesis image is to imagine that slice A alone, with no other breast tissue above or below it, were laid directly on x-ray receptor 12 and imaged. For similar reasons, the same object #2 shows up at different xy locations in FIGS. 3a and 3c.

The new approach described in this patent specification achieves a different result. Given the same data acquisition geometry (FIG. 2), the new approach generates images as illustrated in FIGS. 4b and 4c rather than those of FIGS. 3b and 3c.

Figure 4A:
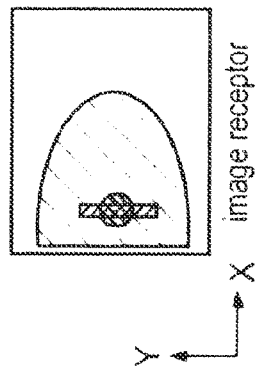
FIGS. 4a, 4b, and 4c illustrate, respectively, a conventional mammogram and two tomosynthesis slice images, where two objects that are at different heights in the breast appear superimposed in the mammogram but at locations in the tomosynthesis slice images that match their locations in the mammogram.

FIG. 4a is the same as FIG. 3a—a mammogram that shows the same objects #1 and #2 superimposed. However, FIG. 4b differs significantly from FIG. 3b, and FIG. 4c differs significantly from FIG. 3c. In particular, FIGS. 4b and 4c show the images of objects #1 and #2 at xy locations that are in the same coordinate system. Moreover, in this example this is the same coordinate system as that of the mammogram of FIGS. 4a (and 3a). Both FIGS. 4b and 3b are tomosynthesis images of slice A, but FIG. 4c shows object #2 in slice image A' at the correct xy location that matches the location of the same object in the mammogram of FIG. 4a. Similarly, both FIGS. 4c and 3c are tomosynthesis images of slice B, but FIG. 4c shows object #2 in slice image B' at the correct xy location that matches the location of the same object in the mammogram of FIG. 4a.

Figure 4B:
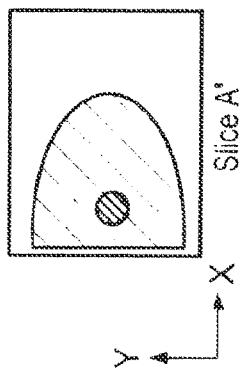
Figure 4C:
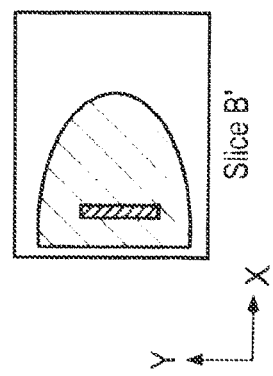
Figures 5A, 5B:
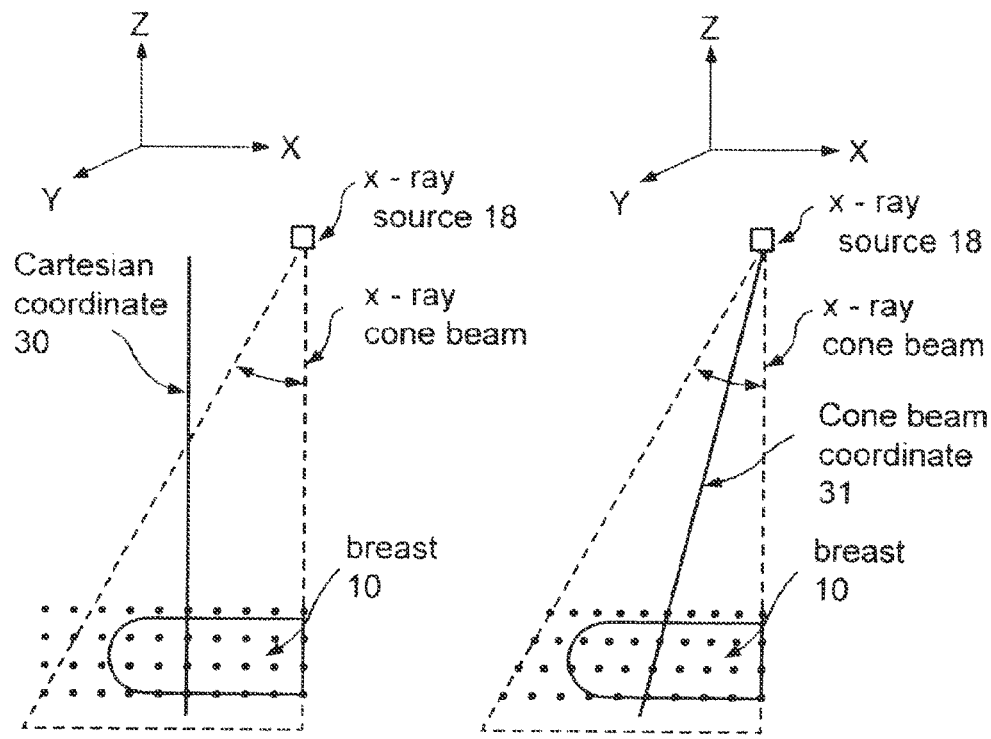
FIGS. 5a and 5b illustrate, respectively, tomosynthesis reconstruction into a Cartesian and into a cone-beam geometry.

The reason for the difference between FIGS. 3b and 4b, and between FIGS. 3c and 4c, is not in how the underlying x-ray measurements are derived but in how the tomosynthesis images are reconstructed and displayed. All relevant x-ray measurements can be obtained as disclosed in said patent application Ser. No. 10/723,486, as one example, typically as respective 2D sets of pixel values (x-ray measurements for elemental picture areas) at each of several different angles of x-ray beam 16 relative to breast 10, e.g. at several equidistant angles over a range of t±15°. Other raw x-ray data acquisition techniques can be used in the alternative. After pre-processing of the type known in the mammography and breast tomosynthesis art, those pixel values can be reconstructed into a rectangular Cartesian coordinate system (30 in FIG. 5a) using known reconstruction algorithms such as filtered back projection, iterative reconstruction, maximum likelihood reconstruction, or others, for example as taught in said patent application Ser. No. 10/723,486. As illustrated in FIG. 5a, the voxels (elemental volume elements) that are imaged as respective pixels in the tomosynthesis slice images are aligned along lines normal to the image plane of receptor 12. The result can be conceptualized as a set of pixel values representing x-ray properties of the voxels that are in the 3D space bound by the image plane of receptor 12 at the bottom, compression paddle 14 on top, and on the sides by the boundaries of x-ray beam 16 that impinges on receptor 12, and are uniformly spaced in xy planes. However, because x-ray beam 16 is cone-shaped or pyramid-shaped, the sides of this 3D space slope at least on three sides of the beam, and the x-ray trajectories from source 18 to receptor 12 diverge in the general case. Thus, in the general case each x-ray trajectory such as trajectory 20 is non-normal to the image plane of receptor 12. As a result, the height of an object in breast 10 influences where the image of that object will be in a mammogram taken with receptor 12. Stated differently, if two objects in the breast are along the same line normal to the image plane, in general they will appear spaced from each other in the mammogram but if the same two objects are along one of the sloping x-ray trajectory, they will appear superimposed in the mammogram. When tomosynthesis reconstruction directly or indirectly calculates a pixel image of a slice that is both parallel to the mammogram image plane and is in the same coordinate system as the mammogram, as disclosed in this patent specification, the resulting tomosynthesis image in general can show the image of an object in the breast at the same position relative to other tissue in the same slice in the breast in all tomosynthesis slice images and will better match the mammogram image.

Conceptually, images such as in FIGS. 4*b* and 4*c* can be obtained by projecting each of several horizontal breast slices separately onto the image plane of the mammography image, along the actual x-ray trajectories included in x-ray beam 16. This can be conceptualized by imagining that a slice such as slice A keeps its physical position illustrated in FIG. 2, all other breast tissue is absent, and a projection image is taken of slice A alone, using the geometry of FIG. 2. Of course, this cannot be done literally because of the presence of breast tissue above and/or below the slice. In the methods and systems disclosed in this patent specification, this result can be achieved directly or indirectly, by implementing a reconstruction algorithm of the type described in the Grant article cited above, adapted to the geometry and other characteristics of a particular x-ray data acquisition system without undue experimentation by a programmer of ordinary skill in the art. For a cone beam x-ray illumination, the reconstruction geometry can be a cone beam coordinate system 31 shown in FIG. 5*b*, where the voxels that correspond to pixels in the tomosynthesis slice images are at different xy spacings (and differ in size at least in the xy plane) in different slices and corresponding voxels of different slices are along the same (generally sloping) x-ray trajectory. Alternatively, the desired result can be achieved indirectly, by first reconstructing tomosynthesis images that together represent a three dimensional space having at least three sloping sides matching the geometry of the imaging x-ray beam (as in the coordinate system of FIG. 5*a*), and then geometrically projecting the pixel values of such tomosynthesis images onto the image plane of the mammogram along the directions of respective x-ray trajectories in the x-ray beam, again using a computer-implemented process adapted without undue experimentation to a particular x-ray data acquisition geometry by a programmer of ordinary skill in the art.

Tomosynthesis slice images such as in FIGS. 4*b* and 4*c* can facilitate assessment of breast features by allowing more direct and simplified comparison between different tomosynthesis slice images and between tomosynthesis slice images on the one hand and conventional mammograms on the other hand. With images such as in FIGS. 4*a*-4*c*, the health professional can read a mammogram (FIG. 4*a*) in a conventional manner, but can also display and view any one or several of a number of tomosynthesis slice images of the same breast to visualize and assess structures that can be at different heights in the breast but appear at the same or at least matching relative locations in each image in which they show. The mammogram and the tomosynthesis slice images can be displayed on the same monitor or screen, displaying one image at a time by alternating from one image to another with a suitable switch or other interface controlled by the health professional. Alternatively, one or more tomosynthesis and/or mammogram images can be displayed on one monitor or screen while one or more other images can be displayed on another monitor or screen, to allow for simultaneous viewing. As another approach, two or more tomosynthesis and/or mammogram images can displayed at respective locations on the same monitor or screen. In each case, a control interface can allow the health professional to select the images for display and the locations for display of those images.

Reconstructing and displaying tomosynthesis slice images (FIGS. 4*b* and 4*c*) as described above is particularly suitable for use in conjunction with computer-aided diagnosis (CAD) of breast images. In CAD, as currently practiced through equipment and/or software provided by companies such as R2 Technology, Inc. of Sunnyvale, Calif., an x-ray breast image is computer-analyzed and image markers are generated and displayed to indicate the location of suspected abnormalities and, in some cases, the likely type of abnormality. When the tomosynthesis slice images are as in FIGS. 4*b* and 4*c*, such markers can be accurately and easily displayed at correct locations relative to the tomosynthesis slice image, even when such markers are generated based solely or mainly on the appropriate mammogram. In addition, fusion images can be generated and selectively displayed under the control of a health professional. For example, a mammogram such as in FIG. 4*a* and a slice image such as in FIG. 4*b* or 4*c* can be superimposed for display, for example with the mammogram in gray scale or in a first selected color or set of colors and the tomosynthesis image in a second selected color or set of colors. The fused image can further include CAD markers displayed at the appropriate locations.

Another display method is to select a region of interest in a mammogram, for example by the health professional drawing or otherwise indicating a region of interest (ROI), and replacing the ROI with the corresponding portion of a selected tomosynthesis slice image. The particular tomosynthesis slice image or succession of such images can be selected by the health professions through an appropriate interface such a track ball or mouse buttons or wheel. The health professional can scroll up and down the height of the imaged breast and see tomosynthesis images within the ROI without losing landmark orientation relative to other parts of the breast that are still seen in the portion of the mammogram outside the ROI. Still in addition, the tomosynthesis x-ray measurements and/or images described above can be used to reconstruct or reformat slice images conforming to planes that are not parallel to the image plane of a mammogram, using image processing techniques known in technologies such as CT (computerized tomography) scanning, and to reconstruct or reformat 3D displays of the imaged breast or selected portions of the breast, for display alone or in conjunction with the display of one or more mammograms and/or 3D tomosynthesis slice images.

Figure 6:
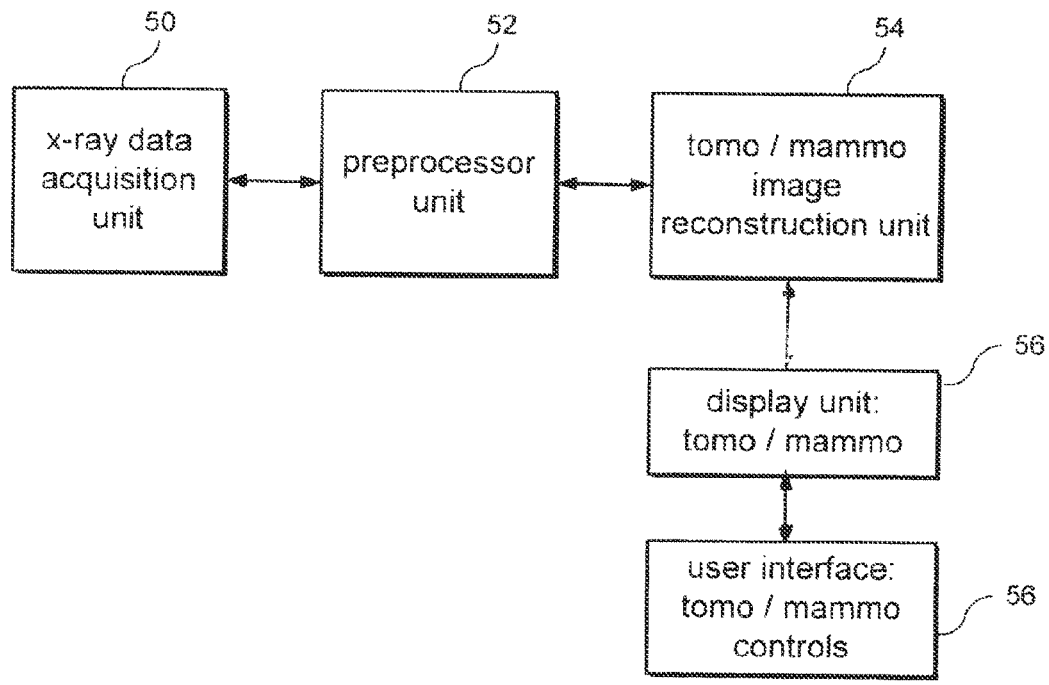
FIG. 6 is a block diagram of a system implementing an example of an embodiment of the disclosed methods and systems.

FIG. 6 illustrates in block diagram form an example of a system implementing technology described above. An x-ray data acquisition unit 50 acquires x-ray measurements for tomosynthesis and/or mammogram images, for example as described in patent application Ser. No. 10/723,486. A pre-processing unit 52 applies known gain and offset corrections to the raw x-ray measurements from unit 50, and known normalization/log conversion of the corrected data. Image reconstruction unit 54 uses the pre-processed x-ray measurements to generate appropriate tomosynthesis and/or mammographic images. Such images are displayed at unit 56, under the control of a user interface 58 that includes controls such a keyboard, mouse, etc. to select and manipulate the displayed images as well as to control units 50-58 for other purposes.

For the reconstruction processing carried out in unit 54, a geometry matrix can be defined from a geometry calibration file and input projection angles appropriate to unit 50 for use in backprojection, from fits to the matrix elements determined from a geometry calibration of unit 50 and input projection angles measured by an encoder in unit 50. Image processing and filtering can be carried out on the images prior to reconstruction, using image processing techniques known in technologies such as CT scanning and tomosynthesis. A known skin line correction can also be applied at this stage. A backprojection can then be carried out, one tomosynthesis slice at a time, using the geometry matrix as follows, $$\begin{pmatrix} u \\ v \\ s \end{pmatrix} = (M_1) \begin{pmatrix} x \\ y \\ z \\ 1 \end{pmatrix} \quad \text{Equation 1}$$

$$d_x = u/s$$
$$d_y = v/s$$

where $M_i$ is the 3×4 geometry matrix for projection i, (x,y,z) is the location of an image pixel, and $(d_x, d_y)$ is the location on the x-ray detector element or area for the line that connects a focal spot in source 18 and the image pixel. This method of backprojection is described, for example, in section 3.4 in Faugeras, O., Three-Dimensional Computer Vision, A Geometric Viewpoint, (MIT Press, 2001), hereby incorporated by reference in this specification.

In a first method, using Cartesian coordinates as in FIG. 5a, the reconstructed slices are parallel to the breast plate, or parallel to the image plane of receptor 12 at 0° projection angle. Voxels and their corresponding image pixels are equally spaced in x-y (in-plane). The x-y pixel spacing is the same for each image slice. The z-pixel spacing is the desired output slice separation. In a second method, using cone beam coordinates as in FIG. 5b, the in-slice pixel spacing varies as a function of slice number, or distance from the focal spot in source 18. The image slices are confined to the volume defined by a given source/detector location, that is, the volume defined by the four lines connecting the x-ray source point to the four corners of image receptor 12 (or any four points on receptor 12). M is first transformed by another matrix to obtain reconstructed planes that are parallel to receptor 12 at some other arbitrary projection angle. This rotation matrix is obtained from the geometry matrix of that projection. In addition, a pixel size scale factor and pixel starting location (corner of a given slice) are calculated for each slice. The scale factor depends on the number of projections that intersect the given pixel. That is, some pixels are not 'seen' by all projections. This scaling reduces band artifacts near the edge of the image.

The tomosynthesis image slices to be reconstructed can be parallel to a "default" reference plane as suggested by Equation 1 above. Alternatively, they can be at other preferred orientations, defined by a 4×4 matrix multiplication operation applied to the original 3×4 matrix M, according to:

$$\begin{pmatrix} u \\ v \\ s \end{pmatrix} = (M_1) \begin{pmatrix} R_{3\times3} & T_3 \\ O_3^T & I_1 \end{pmatrix} \begin{pmatrix} x' \\ y' \\ z' \\ 1 \end{pmatrix} \text{ where } \begin{pmatrix} x \\ y \\ z \\ 1 \end{pmatrix} = \begin{pmatrix} R_{3\times3} & T_3 \\ O_3^T & I_1 \end{pmatrix} \begin{pmatrix} x' \\ y' \\ x' \\ 1 \end{pmatrix} \quad \text{Equation 2}$$

For example, a preferred orientation can be an orientation in which a particular mammogram is taken.

Thus, the backprojection for reconstructing tomosynthesis slice images can involve:

1.) The selection of the orientation of image slices to be reconstructed. The slice can be either parallel to the "default" reference plane as suggested by Equation 1, or at another more preferred orientation, which is defined by a 4×4 matrix multiplication operation to the original 3×4 matrix M, as expressed by Equation 2; and
2.) Selection of the reconstruction voxel grid in space, which can be either a Cartesian grid (FIG. 5a) or a Cone beam grid (FIG. 5b).

It should be clear to those skilled in the relevant technology that the above description is only one example of implementing the new approach and that numerous variations are possible that are within the scope of the description above.

Thus, in one non-limiting example, this patent specification discloses a method comprising: obtaining tomosynthesis x-ray measurements and at least one 2D x-ray projection mammogram of a patient's breast, wherein the mammogram image and the tomosynthesis measurements are obtained using a cone-shaped or pyramid-shaped imaging x-ray beam, and reconstructing 2D tomosynthesis images from the tomosynthesis measurements, wherein the tomosynthesis images conform to the same geometric coordinate system as the 2D projection mammogram, whereby anatomical structures that appear in the mammogram appear at geometrically corresponding places in respective ones of the tomosynthesis images. The step or steps of reconstructing 2D tomosynthesis images can comprise using a computer-implemented cone beam reconstruction algorithm directly generating the tomosynthesis images. Alternatively, the step or steps of reconstructing the 2D tomosynthesis images can comprise generating information describing initial tomosynthesis images, in which tissue or objects in the breast that are at different heights in the breast but overlap in the mammogram appear at mismatched positions in the initial tomosynthesis images, and using the information describing the initial tomosynthesis images to generate final tomosynthesis images in which said tissue or objects appear at positions that match their positions in the mammogram. This alternative can be implemented by generating the initial tomosynthesis images in an initial coordinate system different from that of the mammogram, and processing the information describing the initial tomosynthesis images into tomosynthesis images that match the coordinate system of the mammogram. In the initial coordinate system, the initial tomosynthesis images may differ in pixel spacing while the final tomosynthesis images may have the same pixel spacing. The final pixel spacing may be the same as in the mammogram.

This patent specification also discloses, as another non-limiting example, an x-ray system comprising an x-ray data acquisition unit that uses a cone-shaped or pyramid shaped x-ray beam and an x-ray receptor to obtain tomosynthesis x-ray measurements and x-ray measurements for at least one 2D x-ray projection mammogram of a patient's breast, a pre-processor that receives said measurements from the x-ray receptor and subjects them to pre-processing operations, a tomo/mammo image reconstruction unit that receives the pre-processed images and subjects them to further processing to reconstructing 2D tomosynthesis images and a mammogram, wherein tissue or objects in the breast that are at different heights in the breast but appear superimposed in the mammogram appear at locations in the tomosynthesis images that are the same as or at least match their location in the mammogram, and a display unit that selectively displays one or more of the tomosynthesis images and the mammogram and is under the control of a used interface operated by a health professional. The image reconstruction unit can use a computer-implemented cone beam reconstruction algorithm directly generating the tomosynthesis images. Alternatively, the image reconstruction unit can generate information describing initial tomosynthesis images, in which tissue or objects in the breast that are at different heights in the breast but overlap in the mammogram appear at mismatched positions in the initial tomosynthesis images, and can use the information describing the initial tomosynthesis images to generate final tomosynthesis images in which said objects appear at positions that are the same as or at least match their positions in the mammogram. This alternative can be implemented by generating the initial tomosynthesis images in an initial coordinate system different from that of the mammogram, and processing the information describing the initial tomosynthesis images into tomosynthesis images that match the coordinate system of the mammogram. In the initial coordinate system, the initial tomosynthesis images may differ in pixel spacing while the final tomosynthesis images may have the same pixel spacing. The final pixel spacing may be the same as in the mammogram.

The invention claimed is:

1. A method comprising:
   imaging a breast so as to acquire digital information corresponding to a plurality of 2D x-ray tomosynthesis projection images of the breast taken at different angles;
   generating, from the digital information, a plurality of reconstructed tomosynthesis images representative of respective breast layers;
   obtaining a 2D mammogram image of the breast; and
   displaying at least one of the plurality of reconstructed tomosynthesis images representative of respective breast layers and the 2D mammogram image of the breast.

2. The method of claim 1, wherein the displaying operation includes displaying superimposedly at least two of a plurality of images simultaneously.

3. The method of claim 2, wherein the at least two of the plurality of images includes at least one of the plurality of reconstructed tomosynthesis images representative of respective breast layers and the 2D mammogram image of the breast.

4. The method of claim 2, wherein the displaying operation includes displaying two of the plurality of reconstructed tomosynthesis images representative of respective breast layers.

5. The method of claim 1, wherein each of the plurality of reconstructed tomosynthesis images representative of respective breast layers has a layer thickness corresponding to a thickness of a breast that is less than a total thickness of the breast.

6. The method of claim 1, wherein each of the plurality of reconstructed tomosynthesis images representative of respective breast layers are parallel to an image plane of the 2D mammogram image of the breast.

7. The method of claim 1, wherein the obtaining operation comprises directing an x-ray at the breast.

8. The method of claim 1, wherein at least one of the plurality of the reconstructed tomosynthesis images representative of respective breast layers and the 2D mammogram image of the breast are displayed alternately.

9. The method of claim 1, wherein at least one of the plurality of the reconstructed tomosynthesis images representative of respective breast layers and the 2D mammogram image of the breast are displayed simultaneously.

10. The method of claim 1, wherein at least one of the plurality of the reconstructed tomosynthesis images representative of respective breast layers and the 2D mammogram image of the breast are displayed superimposedly.

11. The method of claim 1, further comprising displaying, based on an input, at least one of the plurality of the reconstructed tomosynthesis images representative of respective breast layers and the 2D mammogram image of the breast.

12. The method of claim 1, further comprising:
   identifying a first location on at least one of the reconstructed tomosynthesis images representative of respective breast layers and a second location on the 2D mammogram image of the breast, wherein both of the first location and the second location correspond to a single predetermined location within the breast.

13. The method of claim 9, further comprising displaying a marker corresponding to the single predetermined location on at least one of the reconstructed tomosynthesis images representative of respective breast layers and the 2D mammogram image of the breast.

14. The method of claim 1, further comprising:
   identifying a location on the 2D mammogram image of the breast; and
   displaying a marker corresponding to the location on at least one of the reconstructed tomosynthesis images representative of respective breast layers.

15. The method of claim 14, wherein the location corresponds to a suspected abnormality.

16. A method comprising:
   displaying a tomosynthesis image representative of a layer of a breast;
   displaying a 2D mammogram image of the breast; and
   superimposing a marker on each of the displayed tomosynthesis image and the displayed 2D mammogram image, wherein the marker corresponds to a single predetermined location within the breast.

17. The method of claim 16, wherein the tomosynthesis image representative of the slice of the breast is parallel to an image plane of the 2D mammogram image of the breast.

18. The method of claim 16, further comprising obtaining digital information regarding at least one of the tomosynthesis image and the 2D mammogram image from an imaging system.

19. The method of claim 16, wherein the tomosynthesis image and the 2D mammogram image are displayed alternately.

20. The method of claim 16, wherein the tomosynthesis image and the 2D mammogram image are displayed simultaneously.

* * * * *